(12) United States Patent
Shirado et al.

(10) Patent No.: US 6,802,845 B2
(45) Date of Patent: Oct. 12, 2004

(54) IMPLANT FOR BONE CONNECTOR

(75) Inventors: Osamu Shirado, Hokkaido (JP); Kazuya Oribe, Tokyo (JP); Hiroshi Takamido, Aichi-ken (JP)

(73) Assignee: Showa Ika Kohgyo Co., Ltd., Aichi (JP)

( * ) Notice: Subject to any disclaimer, the term of this patent is extended or adjusted under 35 U.S.C. 154(b) by 0 days.

(21) Appl. No.: 10/207,911

(22) Filed: Jul. 31, 2002

(65) Prior Publication Data

US 2003/0109882 A1 Jun. 12, 2003

(30) Foreign Application Priority Data

Aug. 1, 2001 (JP) .................................. 2001-233986

(51) Int. Cl.[7] .................... A61B 17/56; A61B 17/58; A61F 2/30
(52) U.S. Cl. ...................................................... 606/61
(58) Field of Search ......................... 606/60, 61, 72, 606/73; 24/342.1, 343, 378.1, 379.1, 527

(56) References Cited

U.S. PATENT DOCUMENTS

| | | | | |
|---|---|---|---|---|
| 5,201,734 A | * | 4/1993 | Cozad et al. | 606/62 |
| 5,415,659 A | * | 5/1995 | Lee et al. | 606/61 |
| 5,439,463 A | * | 8/1995 | Lin | 606/61 |
| 5,487,744 A | * | 1/1996 | Howland | 606/61 |
| 5,527,314 A | * | 6/1996 | Brumfield et al. | 606/61 |
| 5,676,665 A | * | 10/1997 | Bryan | 606/61 |
| 6,050,997 A | * | 4/2000 | Mullane | 606/61 |
| 6,238,396 B1 | * | 5/2001 | Lombardo | 606/61 |
| 6,352,537 B1 | * | 3/2002 | Strnad | 606/61 |
| 6,416,515 B1 | * | 7/2002 | Wagner | 606/61 |
| 6,485,491 B1 | * | 11/2002 | Farris et al. | 606/61 |
| 2002/0169451 A1 | * | 11/2002 | Yeh | 606/61 |

OTHER PUBLICATIONS

"Vertebral Instrumentation", by Sato et al., Medical View, published on May 1, 2002, pp. 63–65, 76–79, and 83–85, with a partial English language translation.

\* cited by examiner

*Primary Examiner*—Eduardo C. Robert
*Assistant Examiner*—Anuradha Ramana
(74) *Attorney, Agent, or Firm*—Greenblum & Bernstein, P.L.C.

(57) ABSTRACT

An implant for bone connector includes a fixing clamp, an implant body, a connecting portion and a movable clamp. The fixing clamp has a curved shape and supports a vertebral arch of a vertebra by grasping the vertebral arch. The implant body is provided on an upper portion of the fixing clamp. The connecting portion with which the connecting member is engaged is provided with the implant body. The movable clamp, which has a curved shape and grasps the vertebral arch, is provided to the implant body and is disposed to be opposed to the fixing clamp.

8 Claims, 6 Drawing Sheets

IMPLANT FOR BONE CONNECTOR

CROSS REFERENCE TO RELATED APPLICATION

This application claims benefit of priority under 35 U.S.C. §119 to Japanese Patent Application No.2001-233986, filed on Aug. 1, 2001, the entire contents of which are incorporated by reference herein.

BACKGROUND OF THE INVENTION

1. Field of the Invention

The present invention relates to an implant for bone connector used for connecting bones, and more particularly, to an implant for bone connector having a connecting portion with which various connecting members are engaged.

2. Description of the Related Art

When connecting bones such as thoracic vertebrae or lumbar vertebrae, the following method has been conventionally employed. A first implant 3 is screwed into centrum 1 such as the thoracic vertebra and the lumbar vertebra. A second implant 4 is screwed into centrum 2. A connecting rod 5 connects the first implant 3 to the second implant 4 as shown in FIG. 1.

The first implant 3 includes a screw portion and a head portion. The screw portion is screwed into centrum and the head portion with a large diameter has a rod engaging groove. Also, the second implant 4 includes the same conformation. Since end portions of the connecting rod 5 are fixed to the rod engaging groove of the first implant 3 and that of the second implant 4 respectively, the connecting rod 5 is integrally fixed to the first implant 3 and the second implant 4 and accordingly a bone connector is formed.

Further, an implant 9 is screwed into centrum 10 separating from the centrum 1 and the centrum 2 for hooking one end of a connecting member 7 such as an artificial ligament. A hook portion 9F is provided on an upper portion of the implant 9, and one end portion of the connecting member 7 is hooked over the hook portion 9F. Another end portion of the connecting member 7 is hooked over a hook portion 5F provided on one top end (the side engaged the first implant 3) of the connection rod 5.

Also, instead of using the connecting rod 5, the connecting member 7 may be used for connecting a first implant to a second implant. A first implant having a hook portion is screwed into the centrum 1, a second implant having a hook portion is screwed into the centrum 2, and both end portions of the connecting member 7 are hooked over the hook portion of the first implant and that of the second implant respectively.

According to the above-described method screwing the implant for bone connector into the centrum for fixing a positional relation between vertebrae, it is necessary to precisely screw the implant into the centrum without damaging other portion. This method requires high technique and a burden of the centrum becomes large, because the implant is screwed into centrum.

SUMMARY OF THE INVENTION

The present invention has been proposed in view of the above-described circumstances, and it is an object of the present invention to provide an implant for bone connector capable of being stably fixed to a vertebral arch of a vertebra without damaging the centrum and to various connecting members.

In order to achieve the above object, the present invention provides an implant for bone connector comprising: a fixing clamp to support a vertebral arch of a vertebra by grasping the vertebral arch; an implant body provided on an upper portion of the fixing clamp; a connecting portion provided to an upper portion of the implant body for engaging a connecting member which connects the implant with another implant; and a movable clamp provided to the implant body and disposed to be opposed to the fixing clamp for grasping the vertebral arch.

According to the present invention, the fixing clamp is provided to a lower portion of the implant body, and supports the vertebral arch of the vertebra by grasping the vertebral arch. The connecting portion is provided on the upper portion of the implant body, and the connecting member is engaged with the connecting portion. The movable clamp is provided to the implant body, is disposed to be opposed to the fixing clamp, and grasps the vertebral arch. Therefore, the implant can grasp the vertebral arch from both sides of the vertebral arch by means of the fixing clamp and the movable clamp, and is engaged with the connecting member. As a result, it is possible to stably fix the implant to the vertebral arch without damaging the centrum, and the implant can be used in the same manner as the conventional implant.

In a preferred embodiment of the present invention, the fixing clamp has a curved shape.

According to the embodiment, even if the fixing clamp has a curved shape, the fixing clamp can be engaged with the vertebral arch. Therefore, it is possible to stable fix the implant to the vertebral arch without damaging the centrum.

In a preferred embodiment of the present invention, the movable clamp can be moved and adjusted in a direction approaching the fixing clamp and separating from the fixing clamp.

According to the embodiment, since the movable clamp can be moved freely in accordance with a size of the vertebral arch, the implant can strongly grasp the vertebral arch from both sides of the vertebral arch by means of the fixing clamp and the movable clamp, and be stably fixed to the vertebral arch.

In a preferred embodiment of the present invention, the movable clamp has a curved shape.

According to the embodiment, even if the movable clamp has a curved shape, the movable clamp can be engaged with the vertebral arch. Therefore, it is possible to stably fix the implant to the vertebral arch without damaging the centrum.

In a preferred embodiment of the present invention, the connecting portion has a rod engaging groove, with a female thread portion, through which the connecting member passes, and has an engaging groove, with a female thread portion, through which the movable clamp passes.

According to the embodiment, it is possible to fix the connecting member and the movable clamp to the connecting portion by means of detent screws.

DESCRIPTION OF THE PREFERRED EMBODIMENTS

Three embodiments of an implant for bone connector according to the present invention will be explained in detail based on the drawings. Constituent elements having the same functions as those of the above-described conventional configuration are designated with the same symbols, and redundant explanation is omitted.

Figure 1:
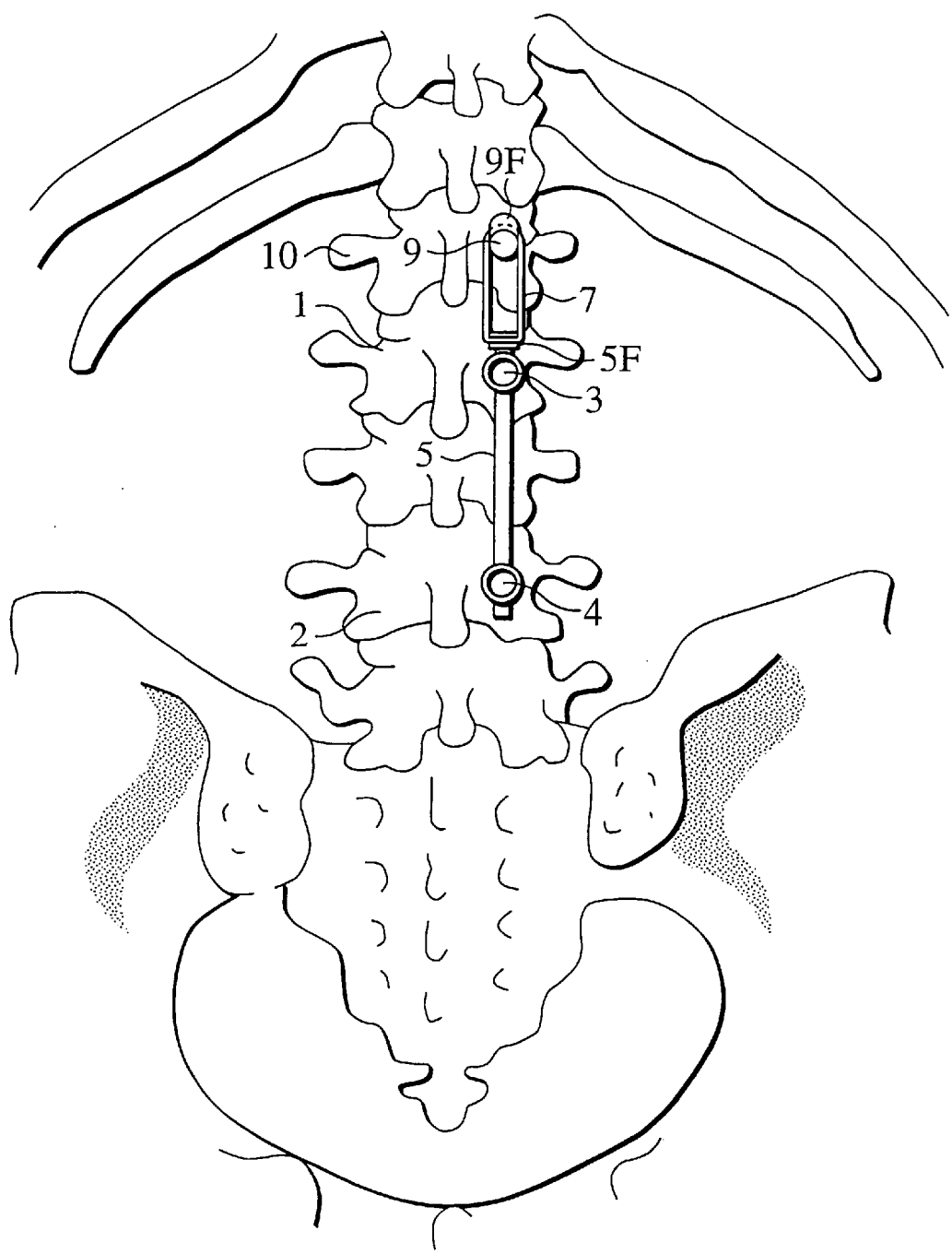
FIG. 1 is a schematic diagram of a conventional implant for bone connector.
Figure 2A:
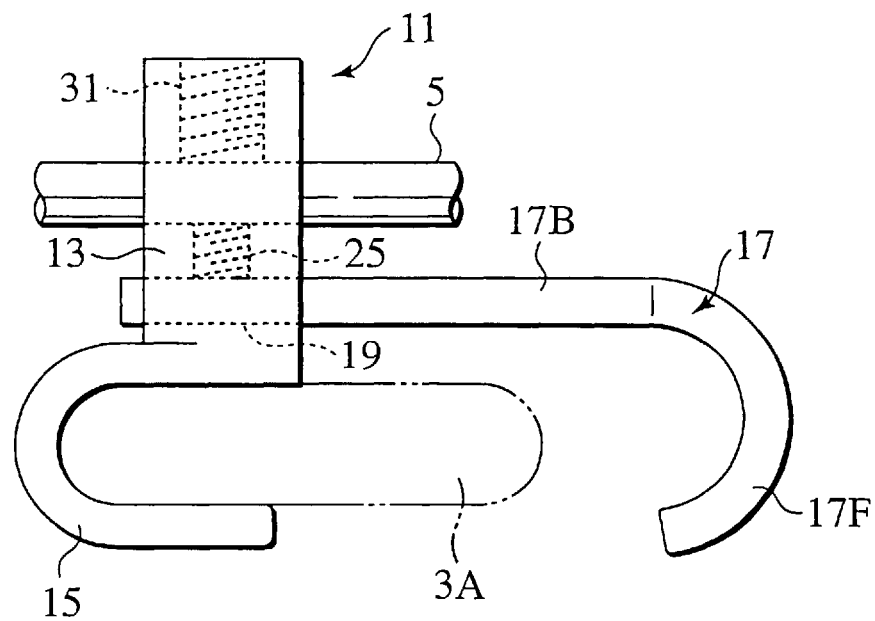
FIGS. 2A and 2B are diagrams of an implant for bone connector according to a first embodiment of the present invention.
Figure 2B:
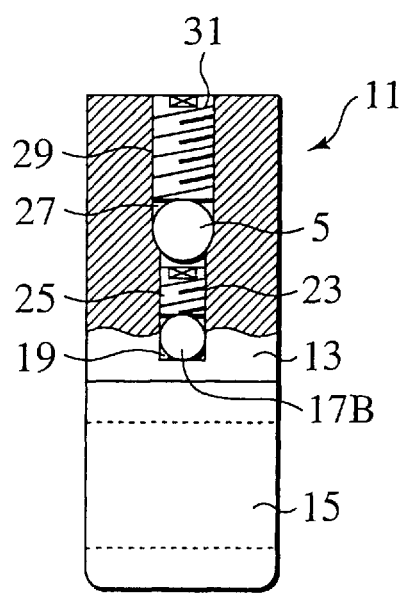

FIGS. 2A and 2B show a first embodiment of the present invention. As shown in FIG. 2A, an implant 11 includes a block-like implant body 13, an U-shaped curved fixing clamp 15, and a movable clamp 17. The implant body 13 has a circular or rectangular cross section and has a connecting portion which is engaged with a connecting member such as connecting rod 5. The fixing clamp 15 is integrally provided to a lower portion of the implant body 13 for supporting a vertebral arch 3A of a vertebra by grasping the vertebral arch 3A. The movable clamp 17 is provided to a lower portion of the implant body 13 for grasping the vertebral arch 3A of the vertebra, and is disposed to be opposed to the fixing clamp 15.

More specific configuration of the lower portion of the implant body is as follows. The movable clamp 17 includes a movable rod-like clamp body 17B and a curved hook portion 17F. As shown FIG. 2B, the movable clamp body 17B is fixed into an engaging groove 19 formed within the implant body 13 by means of a detent screw 25. The hook portion 17F is provided to be opposed to the fixing clamp 15 on a tip end of the clamp body 17B. The hook portion 17F grasps the vertebral arch 3A.

A position of the movable clamp 17 is adjusted in a direction approaching the fixing clamp 15 and separating from that for grasping the vertebral arch 3A. Also, it is possible to rotate and adjust the movable clamp 17 around an axis of the rod-like clamp body 17B. In order to fix the movable clamp 17 in the position fitting to a size of the vertebral arch 3A, a female thread portion 23 is formed on a surface of the engaging groove 19. Therefore, the movable clamp 17 is fixed in a proper position by screwing the detent screw 25 into the female thread portion 23. As a result, it is possible to adjust the movable clamp 17 to the desired position.

A rod engaging groove 27 to be fixed to the connection rod 5 is formed at an upper portion of the engaging groove 19. A width of the rod engaging groove 27 is slightly greater than that of the engaging groove 19. A female thread portion 29 is formed on a surface of the rod engaging groove 27. A detent screw 31 for fixing the connection rod 5 to the implant body 13 is screwed into the female thread portion 29.

With the above configuration, the fixing clamp 15 supports the vertebral arch 3A by grasping the vertebral arch 3A, and the hook portion 17F of the movable clamp 17 grasps the vertebral arch 3A. Therefore, the implant 11 can grasp the vertebral arch 3A from both sides of the vertebral arch 3A by means of the fixing clamp 15 and the movable clamp 17. Thereby it is possible to stably fix implant 11 to the vertebral arch 3A without damaging the centrum. At that time, it is easy to fix the implant 11 to the vertebral arch 3A, because the detent screw 25 can be rotated and operated without interruption of vertebra and another implant by means of a tool for screwing the detent screw 25 into the female thread portion 23 from the upper direction of the female thread portion 23.

As described above, after the implant 11 is fixed to the vertebral arch 3A in this manner, the connection rod 5 is fixed to the rod engaging groove 27 by screwing the detent screw 31 into the female thread portion 29, thereby the connection rod 5 is fixed to the implant 11.

In the above-explained embodiment, the movable clamp 17 and the connection rod 5 are fixed to the implant body 13, and the engaging groove 19 and the rod engaging groove 27 are formed in the implant body 13 such as to open upward. Alternatively, holes through which the movable clamp 17 and the connection rod 5 pass may be formed horizontally, and accordingly female thread portions into which the detent screws 25 and 31 are screwed may be formed to each upper potion of the former hole.

It is also possible to form a male thread in an outer peripheral surface of the implant body 13, and to screw a nut member into the male thread for fixing the movable clamp 17 and the connecting rod 5 to implant body 13. At that time, using the clamp body 17B of the movable clamp 17, it is also possible to provide a long hole in the clamp body 17B through which the implant body 13 can pass such as to sandwich the implant body 13, and it is also possible to make the clamp body 17B as a bifurcated configuration.

Figure 3A:
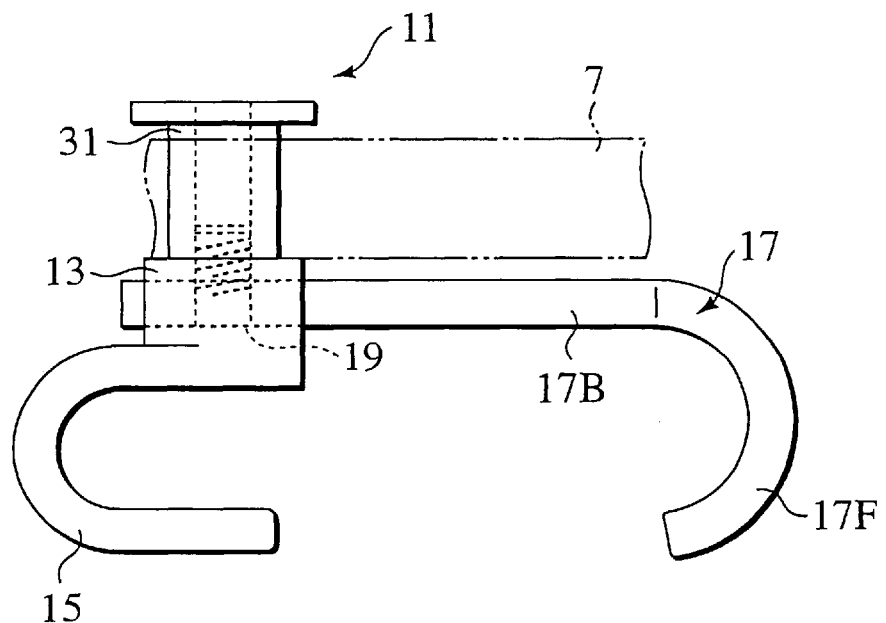
FIGS. 3A and 3B are diagrams of an implant for bone connector according to a second embodiment of the present invention.
Figure 3B:
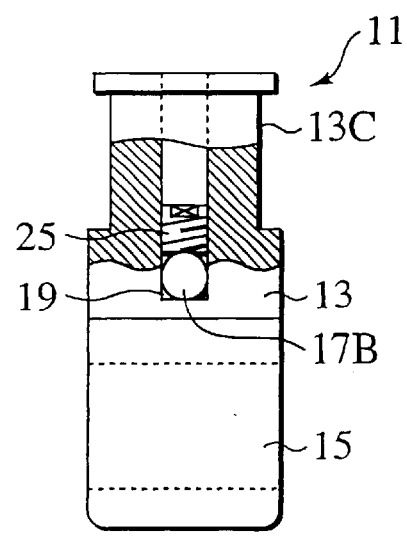

FIGS. 3A and 3B show a second embodiment of the present invention. In this embodiment, an annular recess 13C is formed on a connecting portion with which a connecting member 7 is engaged, and the connecting member 7 such as artificial ligament, wire or cable instead of the connection rod 5 may be used. Other configuration is the same as that of the previous embodiment, constituent elements having the same functions are designated with the same symbols, and redundant explanation is omitted.

Figure 4:
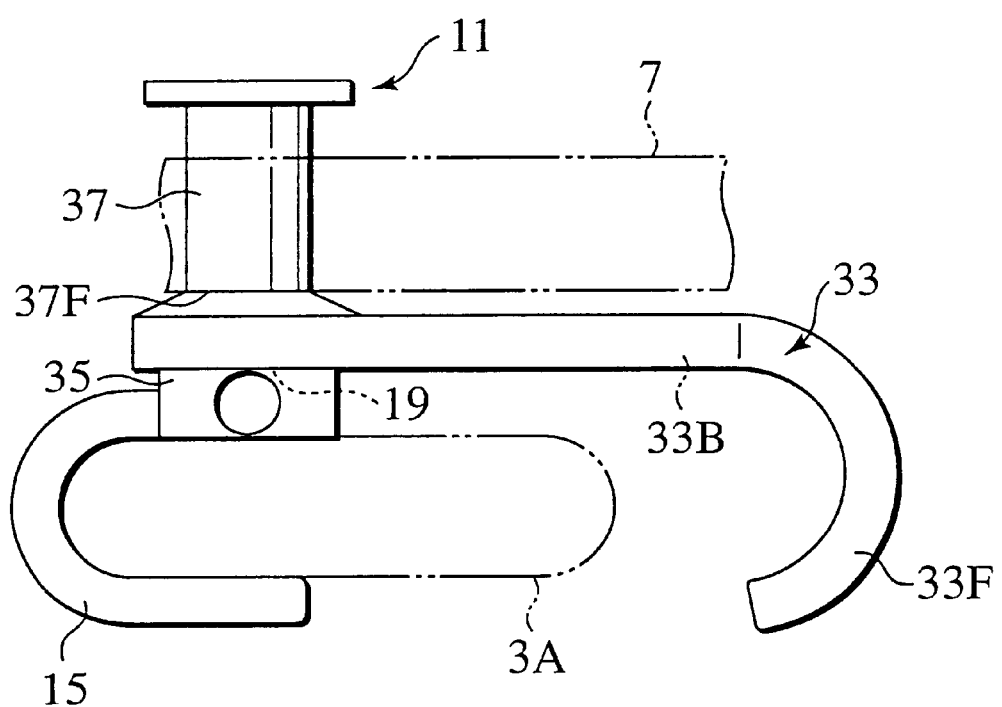
FIG. 4 is a diagram of an implant for bone connector according to a third embodiment of the present invention.
Figure 5:
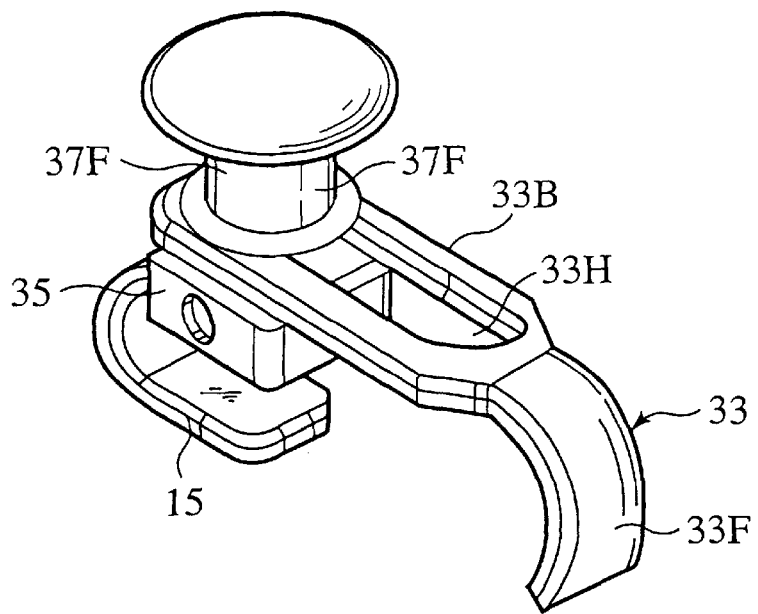
FIG. 5 is a perspective diagram of the implant for bone connector according to the third embodiment of the present invention.
Figure 6:
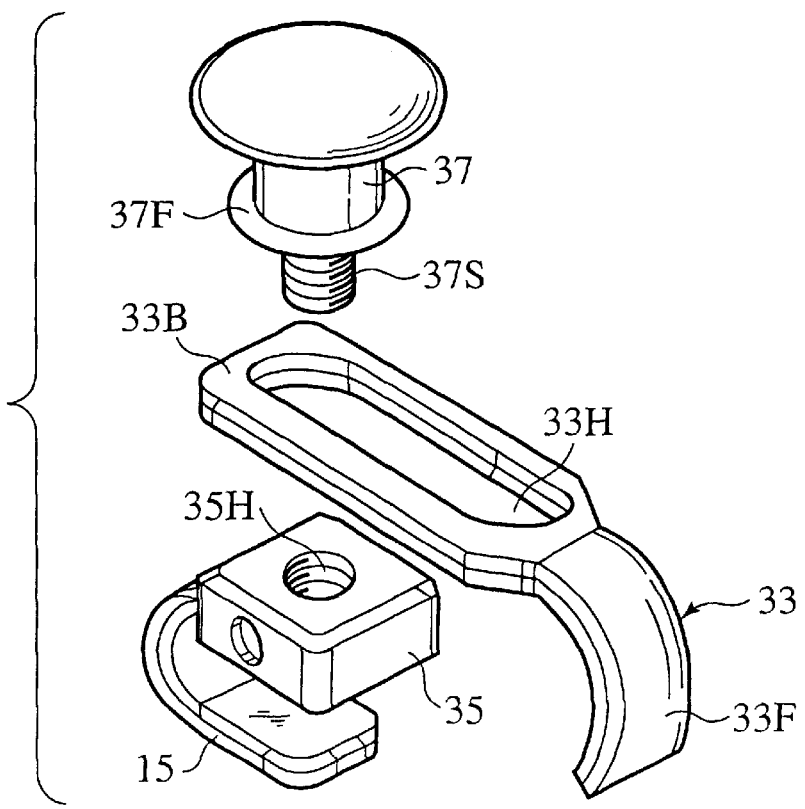
FIG. 6 is an exploded perspective diagram of the implant for bone connector according to the third embodiment of the present invention.

FIGS. 4 to 6 show a third embodiment of the present invention. In an implant 11 of this embodiment, a movable clamp 33, which is disposed to be opposed to the fixing clamp 15 and which grasps the vertebral arch 3A, is provided on an upper portion of the implant body 35. The movable clamp 33 can be freely slid and turned or fixed.

More specifically, as shown in FIG. 6, a thread hole 35H is formed on an upper surface of the implant body 35 having the fixing clamp 15, and a thread portion 37S which is screwed into the thread hole 35H is provided on a lower portion of the hook portion 37. The movable clamp 33 includes a curved hook portion 33F on a tip end of a clamp body 33B. The clamp body 33B of the movable clamp 33 has a slit or a long hole 33H. Since the movable clamp 33 is disposed to be opposed to the fixing clamp 15, the hook portion 33F grasps the vertebral arch 3A of the vertebral arch at the opposite side of the fixing clamp 15.

In the above configuration, as shown in FIG. 6, the clamp body 33B of the movable clamp 33 is disposed between the implant body 35 and the hook portion 37 and then, the thread portion 37S of the hook portion 37 is allowed to pass through the long hole 33H formed in the clamp body 33B and to be screwed into the thread hole 35H of the implant body 35. Then, the movable clamp 33 is sandwiched between the implant body 35 and the hook portion 37.

In a state in which the movable clamp 33 is softly sandwiched between the implant body 35 and the hook portion 37, the movable clamp 33 can be moved and adjusted in a direction approaching the fixing clamp 15 and separating from that, and the movable clamp 33 can be rotated and adjusted around the thread portion 37S of the hook portion 37. Therefore, the movable clamp 33 can be adjusted to a size of the vertebral arch 3A. If the thread portion 37S of the hook portion 37 is strongly fastened to the thread hole 35H, the clamp body 33B of the movable clamp 33 is strongly sandwiched and fixed between the implant body 35 and a lower flange 37F provided on a lower portion of the hook portion 37. Therefore, the implant 11 can firmly grasp the vertebral arch 3A from both sides of the vertebral arch 3A by means of the fixing clamp 15 and the movable clamp 33. That is, in this embodiment, the hook portion 37 serves as a hook over which the connecting member 17 is hooked, and as a fixing tool for fixing the movable clamp 33.

Since the implant 11 firmly grasps the vertebral arch 3A from both of sides of the vertebral arch 3A by means of the fixing clamp 15 and the movable clamp 33, the implant 11 can be fixed to the centrum. Therefore, the same effect as the implant 11 of the first and the second embodiments can be obtained, and the implant 11 can be fixed to the centrum more stably.

Figure 7:
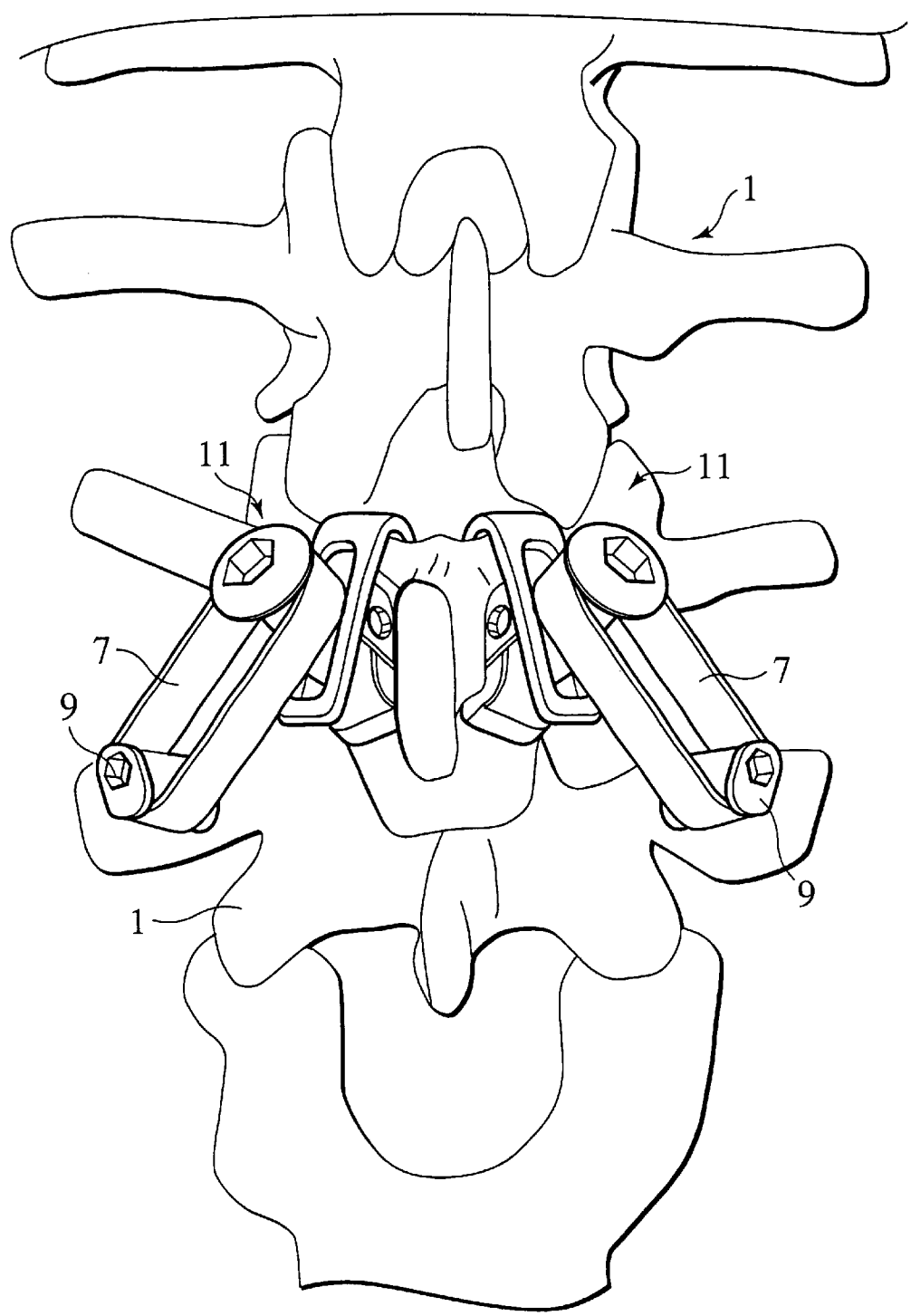
FIG. 7 is a diagram showing one using example of the present invention.

FIG. 7 shows one example in which the connecting member 7 is hooked over the implant 11 and the implant 9. In this case, the implant 9 which is screwed into centrum is used instead of the implant 11.

The above-described embodiment is one example of the present invention. Thus, the present invention is not limited to the above embodiment, and various modifications can be made in accordance with configuration within a range not departing from technical idea of the invention.

That is, although both the fixing clamp and moving clamp have curved shapes respectively in the three embodiments, the present invention is not limited to this, and the invention can be applied only if the vertebral arch 3A of the vertebra can be grasped.

What is claimed is:

1. An implant for bone connector comprising:
   a fixing clamp to support a vertebral arch of a vertebra by grasping the vertebral arch;
   an implant body provided on an upper portion of the fixing clamp;
   a movable clamp disposed to be opposed to the fixing clamp for grasping the vertebral arch; and
   a connecting portion provided in the implant body for engaging the movable clamp and a connecting member to the implant body, the connecting member connecting the implant with another implant; and
   wherein the connecting portion has a rod engaging groove, with a female thread portion, through which the connecting member passes, and has an engaging groove, with a female thread portion, through which the movable clamp passes.

2. An implant for bone connector according to claim 1, wherein the fixing clamp has a curved shape.

3. An implant for bone connector according to claim 1, wherein the movable clamp can be moved and adjusted in a direction approaching the fixing clamp and separating from the fixing clamp.

4. An implant for bone connector according to claim 3, wherein the movable clamp has a curved shape.

5. An implant for bone connector comprising:
   a fixing clamp to support a vertebral arch of a vertebra by grasping the vertebral arch;
   an implant body provided on an upper portion of the fixing clamp;
   a movable clamp disposed to be opposed to the fixing clamp for grasping the vertebral arch;
   a connecting portion provided in the implant body for engaging the movable clamp to the implant body; and
   a recess portion provided on an upper portion of the implant body for engaging a connecting member to the implant body, the connecting member connecting the implant with another implant;
   wherein the connecting portion has an engaging groove, with a female thread portion, through which the movable clamp passes.

6. An implant for bone connector according to claim 5, wherein the fixing clamp has a curved shape.

7. An implant for bone connector according to claim 5, wherein the movable clamp can be moved and adjusted in a direction approaching the fixing clamp and separating from the fixing clamp.

8. An implant for bone connector according to claim 7, wherein the movable clamp has a curved shape.

* * * * *

UNITED STATES PATENT AND TRADEMARK OFFICE
CERTIFICATE OF CORRECTION

PATENT NO. : 6,802,845 B2
DATED : October 12, 2004
INVENTOR(S) : O. Shirado et al.

It is certified that error appears in the above-identified patent and that said Letters Patent is hereby corrected as shown below:

Title page,
Item [56], References Cited, U.S. PATENT DOCUMENTS, should include:
-- 4,085,744   04/25/78   Lewis et al.
   6,077,263   06/20/00   Ampeil et al. --
FOREIGN PATENT DOCUMENTS, should include:
-- 2269753    02/23/94   United Kingdom
   2662073    11/22/91   France
   2684866    06/18/93   France
   2695550    03/18/94   France
   2752719    03/06/98   France
   1011260    08/11/00   Netherlands
   9-285473   11/04/97   Japan
   11-89854   04/06/99   Japan
   11347046   12/21/99   Japan --
OTHER PUBLICATIONS, should include:
-- English Language Abstract of JP 9-285473.
   English Language Abstract of JP 11-347046. --

Column 6,
Line 6, after "implant" delete "and".

Signed and Sealed this

Twenty-first Day of June, 2005

JON W. DUDAS
*Director of the United States Patent and Trademark Office*